(12) United States Patent
Baril et al.

(10) Patent No.: US 11,864,815 B2
(45) Date of Patent: Jan. 9, 2024

(54) ELECTROSURGICAL DEVICE FOR CUTTING TISSUE

(71) Applicant: Covidien LP, Mansfield, MA (US)

(72) Inventors: Jacob C. Baril, Norwalk, CT (US); Saumya Banerjee, Hamden, CT (US); Amy Kung, Hamden, CT (US); Christopher M. Meehan, Shelton, CT (US); Thomas A. Zammataro, North Haven, CT (US); Brian J. Creston, Shelton, CT (US); Scott J. Prior, Shelton, CT (US); Ernest A. Addi, Middletown, CT (US); Matthew A. Dinino, Newington, CT (US); Ronald L. Green, Bethel, CT (US)

(73) Assignee: Covidien LP, Mansfield, MA (US)

(*) Notice: Subject to any disclaimer, the term of this patent is extended or adjusted under 35 U.S.C. 154(b) by 730 days.

(21) Appl. No.: 16/783,417

(22) Filed: Feb. 6, 2020

(65) Prior Publication Data
US 2021/0244461 A1    Aug. 12, 2021

(51) Int. Cl.
*A61B 18/14* (2006.01)
*A61B 18/00* (2006.01)
*A61B 18/12* (2006.01)

(52) U.S. Cl.
CPC .......... *A61B 18/14* (2013.01); *A61B 18/1402* (2013.01); *A61B 2018/00083* (2013.01);
(Continued)

(58) Field of Classification Search
CPC ...... A61B 2018/144; A61B 2018/1412; A61B 218/1407; A61B 18/1402; A61B 18/14;
(Continued)

(56) References Cited

U.S. PATENT DOCUMENTS 2,022,065 A    11/1935   Wappler
2,047,535 A    7/1936    Wappler
(Continued)

FOREIGN PATENT DOCUMENTS

WO    2016025132 A1    2/2016

OTHER PUBLICATIONS

U.S. Appl. No. 16/540,593 to Baril et al.

*Primary Examiner* — Sean W Collins
(74) *Attorney, Agent, or Firm* — Carter, DeLuca & Farrell LLP

(57) ABSTRACT

An electrosurgical device for cutting tissue includes a body portion and a tool portion extending distally from the body portion. The tool portion defines a longitudinal axis. The tool portion includes a return lead adapted to be electrically coupled to a return terminal of an electrosurgical energy source, first and second electrical insulators disposed on a first surface of the return lead, and an active lead adapted to be electrically coupled to an active terminal of the electrosurgical energy source. The first electrical insulator is disposed distal of the second electrical insulator. The active lead extends through the first and second electrical insulators such that the active lead and the first surface of the return lead define a gap therebetween. Upon activation of the electrosurgical energy source, electrosurgical energy is transmitted from the active lead through tissue to the return lead to cut the tissue.

20 Claims, 7 Drawing Sheets

(52) U.S. Cl.
CPC ............ *A61B 2018/00178* (2013.01); *A61B 2018/00601* (2013.01); *A61B 2018/00607* (2013.01); *A61B 2018/126* (2013.01); *A61B 2018/144* (2013.01); *A61B 2018/1407* (2013.01); *A61B 2018/1467* (2013.01)

(58) Field of Classification Search
CPC  A61B 2018/00083; A61B 2018/00607; A61B 2018/126; A61B 2018/1467
See application file for complete search history.

(56) References Cited

U.S. PATENT DOCUMENTS

| | | | |
|---|---|---|---|
| 3,516,412 A | 6/1970 | Ackerman | |
| 3,886,944 A | 6/1975 | Jamshidi | |
| 4,161,950 A | 7/1979 | Doss et al. | |
| 4,196,734 A | 4/1980 | Harris | |
| 4,198,957 A | 4/1980 | Cage et al. | |
| 4,485,810 A | 12/1984 | Beard | |
| 4,534,347 A | 8/1985 | Taylor | |
| 4,622,966 A | 11/1986 | Beard | |
| 4,633,880 A | 1/1987 | Osypka et al. | |
| 4,862,890 A | 9/1989 | Stasz et al. | |
| 5,013,312 A | 5/1991 | Parins et al. | |
| 5,085,659 A | 2/1992 | Rydell | |
| 5,300,068 A | 4/1994 | Rosar et al. | |
| 5,360,428 A | 11/1994 | Hutchinson, Jr. | |
| 5,441,499 A | 8/1995 | Fritzsch | |
| 5,531,744 A | 7/1996 | Nardella et al. | |
| 5,536,267 A | 7/1996 | Edwards et al. | |
| 5,578,048 A | 11/1996 | Pasqualucci et al. | |
| 5,599,295 A | 2/1997 | Rosen et al. | |
| 5,599,346 A | 2/1997 | Edwards et al. | |
| 5,611,798 A | 3/1997 | Eggers | |
| 5,647,372 A | 7/1997 | Tovey et al. | |
| 5,681,282 A * | 10/1997 | Eggers ............... | A61B 18/1485 604/114 |
| 5,766,167 A | 6/1998 | Eggers et al. | |
| 6,027,501 A | 2/2000 | Goble et al. | |
| 6,217,528 B1 | 4/2001 | Koblish et al. | |
| 6,494,881 B1 | 12/2002 | Bales et al. | |
| 6,530,924 B1 | 3/2003 | Ellman et al. | |
| 6,533,781 B2 | 3/2003 | Heim et al. | |
| 6,752,767 B2 | 6/2004 | Turovskiy et al. | |
| 7,033,354 B2 | 4/2006 | Keppel | |
| 7,156,844 B2 | 1/2007 | Reschke et al. | |
| 7,371,234 B2 | 5/2008 | Young | |
| 7,399,299 B2 | 7/2008 | Daniel et al. | |
| 7,419,488 B2 | 9/2008 | Ciarrocca et al. | |
| 7,846,108 B2 | 12/2010 | Turovskiy et al. | |
| 7,846,158 B2 | 12/2010 | Podhajsky | |
| 8,137,345 B2 | 3/2012 | McNall, III et al. | |
| 8,734,464 B2 | 5/2014 | Grover et al. | |
| 8,777,961 B2 | 7/2014 | Cabrera et al. | |
| 8,968,301 B2 | 3/2015 | Weber | |
| 8,968,329 B2 | 3/2015 | Cabrera | |
| 9,060,765 B2 | 6/2015 | Rencher et al. | |
| 9,358,065 B2 | 6/2016 | Ladtkow et al. | |
| 9,445,863 B2 | 9/2016 | Batchelor et al. | |
| 9,549,747 B2 | 1/2017 | Carlson | |
| 9,592,067 B2 | 3/2017 | Hartoumbekis | |
| 9,775,665 B2 | 10/2017 | Ellman | |
| 9,987,031 B2 | 6/2018 | Menn | |
| 9,993,229 B2 | 6/2018 | Whitfield | |
| 9,993,287 B2 | 6/2018 | Sartor et al. | |
| 10,034,661 B2 | 7/2018 | Holsten et al. | |
| 10,045,761 B2 | 8/2018 | Weber | |
| 10,154,833 B2 | 12/2018 | Holsten et al. | |
| 10,376,314 B2 | 8/2019 | van der Weide et al. | |
| 10,433,898 B2 | 10/2019 | Borgmeier et al. | |
| 10,433,899 B2 | 10/2019 | Borgmeier et al. | |
| 10,531,917 B2 | 1/2020 | Johnson et al. | |
| 2004/0153057 A1* | 8/2004 | Davison ............. | A61B 18/1206 604/35 |
| 2005/0070895 A1 | 3/2005 | Ryan et al. | |
| 2005/0107777 A1* | 5/2005 | West .................. | A61B 18/1402 606/41 |
| 2005/0131402 A1* | 6/2005 | Ciarrocca .......... | A61B 18/1482 606/41 |
| 2005/0283149 A1 | 12/2005 | Thorne et al. | |
| 2007/0078454 A1 | 4/2007 | McPherson | |
| 2007/0118110 A1 | 5/2007 | Girard et al. | |
| 2007/0149966 A1 | 6/2007 | Dahla et al. | |
| 2007/0179494 A1 | 8/2007 | Faure | |
| 2007/0219546 A1 | 9/2007 | Mody et al. | |
| 2007/0260240 A1 | 11/2007 | Rusin | |
| 2007/0265609 A1 | 11/2007 | Thapliyal et al. | |
| 2008/0281323 A1 | 11/2008 | Burbank et al. | |
| 2009/0306642 A1 | 12/2009 | Vankov | |
| 2012/0116416 A1 | 5/2012 | Neff et al. | |
| 2013/0255063 A1 | 10/2013 | Hart et al. | |
| 2013/0267947 A1 | 10/2013 | Orszulak | |
| 2019/0083172 A1 | 3/2019 | Ladtkow et al. | |
| 2019/0099599 A1* | 4/2019 | Kreindel ................ | A61N 1/36 |
| 2019/0321018 A1 | 10/2019 | Prior | |

* cited by examiner

ELECTROSURGICAL DEVICE FOR CUTTING TISSUE

FIELD

The present disclosure relates to surgical instruments and, more particularly, to bipolar electrosurgical instruments for cutting tissue.

BACKGROUND

Laparoscopic surgery is increasingly common. The principle of laparoscopic surgery is to perform a surgical procedure with small keyhole incisions. Usually, two or three such keyhole incisions are made in the abdomen for insertion of a telescopic video camera, laparoscopic instruments, and/or electrosurgical devices. Electrosurgical devices are used in both open surgical and laparoscopic surgical procedures to cut and/or coagulate tissue. Various types of electrosurgical devices are known, including those that use diathermy with either monopolar or bipolar current, and advanced devices such as harmonic scissors and argon beam and laser devices. Monopolar and bipolar devices use one or two electrodes, respectively, to deliver electrical energy from a current source to the surgical site. By varying the voltage, current, or waveform of the electrical energy delivered by the electrode, surgeons can cut tissue, coagulate tissue to stop bleeding, or produce a "blended cut" that combines these two functions.

SUMMARY

As used herein, the term "distal" refers to the portion that is being described which is further from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In accordance with an aspect of the present disclosure, an electrosurgical device for cutting tissue includes a body portion and a tool portion extending distally from the body portion. The tool portion defines a longitudinal axis. The tool portion includes a return lead adapted to be electrically coupled to a return terminal of an electrosurgical energy source, first and second electrical insulators disposed on a first surface of the return lead, and an active lead adapted to be electrically coupled to an active terminal of the electrosurgical energy source. The first electrical insulator is disposed distal of the second electrical insulator. The active lead extends through the first and second electrical insulators such that the active lead and the first surface of the return lead define a gap therebetween. Upon activation of the electrosurgical energy source, electrosurgical energy is transmitted from the active lead through tissue to the return lead to cut tissue.

In an aspect of the present disclosure, the first surface of the return lead may define an acute angle with respect to the longitudinal axis of the tool portion.

In another aspect of the present disclosure, the first and second electrical insulators may be parallel to the longitudinal axis of the tool portion.

In yet another aspect of the present disclosure, the return lead may include a nose portion configured to engage tissue. The nose portion may be adjacent the second electrical insulator.

In still another aspect of the present disclosure, the nose portion may include a blunt tip.

In still yet another aspect of the present disclosure, the active lead may be a wire.

In another aspect of the present disclosure, the active lead may be a single strand wire.

In another aspect of the present disclosure, the return lead may further include a second nose portion adjacent the first electrical insulator. The second nose portion may be configured to engage tissue.

In yet another aspect of the present disclosure, the first or second electrical insulator may have a tubular configuration.

In still yet another aspect of the present disclosure, the first or second electrical insulator may be formed of ceramic.

In still yet another aspect of the present disclosure, the return lead may be formed of stainless steel.

In still yet another aspect of the present disclosure, the tool portion may further include first and second supports configured to be securely received in the respective first and second electrical insulators.

In still yet another embodiment, the first and second supports may be configured to support the active lead extending therethrough.

In accordance with another aspect of the present disclosure, an electrosurgical device for cutting tissue includes a body portion configured to be operatively coupled to an electrosurgical energy source and a tool portion extending distally from the body portion. The tool portion defines a longitudinal axis. The tool portion includes an active lead adapted to be electrically coupled to a first electrical potential of the electrosurgical energy source, a return lead adapted to be electrically coupled to a second electrical potential of the electrosurgical energy source, a first pair of electrical insulators disposed on a first surface of the return lead, and a second pair of electrical insulators disposed on the second surface of the return lead. The active lead includes first and second segments. At least one of the first or second surfaces defines an acute angle with respect to the longitudinal axis of the tool portion. The first pair of electrical insulators is configured to receive the first segment of the active lead therethrough. The second pair of electrical insulators is configured to receive the second segment of the active lead therethrough. Upon activation of the electrosurgical energy source, electrosurgical energy is transmitted between electrical potentials and through tissue disposed therebetween.

In an aspect of the present disclosure, the first and second surfaces of the tool portion may be symmetric with respect to the longitudinal axis.

In another aspect of the present disclosure, at least one of the first or second segments of the active lead may define an acute angle with respect to the longitudinal axis.

In still another aspect of the present disclosure, the electrical insulators of at least one of the first or second pair of electrical insulators may be formed of ceramic.

In an aspect of the present disclosure, the electrical insulators of at least one of the first or second pair of electrical insulators may be parallel with the longitudinal axis.

In another aspect of the present disclosure, at least one of the first or second segments of the active lead may define a gap with the respective first or second surfaces of the tool portion.

In yet another aspect of the present disclosure, the body portion of the electrosurgical device may include a switch to selectively supply electrosurgical energy to the active lead.

In still yet another aspect of the present disclosure, the active lead may be a wire.

In accordance with an aspect of the present disclosure, an electrosurgical device for cutting tissue includes a body portion and a tool portion extending distally from the body portion. The body portion defines a longitudinal axis. The tool portion includes a return lead, first and second insulators (e.g., electrical insulators, although electrical and thermal insulators are also contemplated), and an active lead. The return lead is adapted to be electrically coupled to a return terminal of an electrosurgical energy source. The return lead defines a recess between proximal and distal portions thereof. The first and second insulators are disposed on the respective proximal and distal portions of the return lead. The active lead extends through the first and second insulators and across the recess of the return lead. Upon activation of the electrosurgical energy source, electrosurgical energy is transmitted from the active lead through tissue in contact with the active lead to the return lead to cut the tissue in contact with the active lead.

In an aspect of the present disclosure, a portion of the active lead extending across the recess of the return lead may be parallel to the longitudinal axis.

In another aspect of the present disclosure, the second insulator may have a conical profile and define a bore therethrough.

In yet another aspect of the present disclosure, a distal portion of the active lead may include a ferrule configured to be nested within the second insulator.

In still another aspect of the present disclosure, the distal portion of the return lead may have a blade portion configured to mechanically cut tissue.

In still yet another aspect of the present disclosure, the active lead may be a wire.

In another aspect of the present disclosure, the active lead may be a single strand wire.

In another aspect of the present disclosure, the proximal portion of the return lead may include a nose portion adjacent the first insulator.

In yet another aspect of the present disclosure, the nose portion may have a blunt tip configured to engage tissue.

In still yet another aspect of the present disclosure, the first or second insulator may be formed of ceramic.

In still yet another aspect of the present disclosure, the return lead may be formed of stainless steel.

In still yet another aspect of the present disclosure, the body portion may further include a tensioner rotatably associated with the active lead to adjust tension in the active lead.

In accordance with another aspect of the present disclosure, an electrosurgical device for cutting tissue includes a body portion and a tool portion extending distally from the body portion. The tool portion defines a longitudinal axis. The tool portion includes an active lead adapted to be electrically coupled to a first electrical potential of an electrosurgical energy source, a return lead adapted to be electrically coupled to a second electrical potential of the electrosurgical energy source, and first and second electrical insulators secured with distal and proximal portions the return lead, respectively. The return lead defines a recess therebetween. A distal portion of the active lead is secured with the first electrical insulator and a proximal portion of the active lead is operatively coupled with the body portion. Upon activation of the electrosurgical energy source, electrosurgical energy is transmitted between electrical potentials and through tissue disposed therebetween to cut tissue in contact with the active lead.

In an aspect of the present disclosure, the active lead may be a wire.

In another aspect of the present disclosure, the body portion may include a tensioner configured to adjust tension of the wire.

In still another aspect of the present disclosure, the second electrical insulator may have a tubular shape.

In an aspect of the present disclosure, the first electrical insulator may have a conical shape defining a bore therethrough such that the distal portion of the active lead is nested within the first electrical insulator.

In another aspect of the present disclosure, the distal portion of the return lead may include a blade adjacent the first electrical insulator.

In yet another aspect of the present disclosure, the body portion may include a switch to selectively supply electrosurgical energy to the active lead.

In still yet another aspect of the present disclosure, the proximal portion of the return lead may include a nose portion including a blunt tip adjacent the second electrical insulator.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
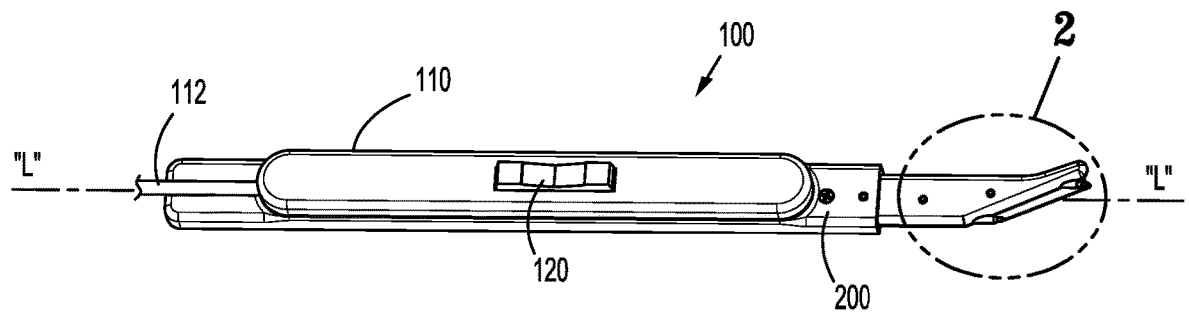
FIG. 1 is a perspective view of an electrosurgical device in accordance with an aspect of the present disclosure.

Turning now to FIG. 1, an electrosurgical device in accordance with an aspect of the present disclosure is generally shown as an electrosurgical device 100 adapted to be electrically coupled to an electrosurgical energy source such as, e.g., a generator (not shown), to provide bipolar radio-frequency (RF) power output. The electrosurgical energy source may include electronic circuitry configured to generate radio frequency energy specifically suited for various electrosurgical modes and/or procedures. The electrosurgical energy source may include one or more converting devices for converting from DC to AC or vice versa. The electrosurgical device 100 may be configured to transmit any suitable electric current (e.g., AC and/or DC) at any suitable frequency. For a detailed discussion of the construction and operation of exemplary electrosurgical devices and electrosurgical energy sources, reference may be made to U.S. Patent Publication Nos. 2013/0267947 and 2013/0255063; and U.S. Pat. Nos. 7,156,844 and 5,766,167, the entire contents of each of which are incorporated by reference herein.

Figure 2:
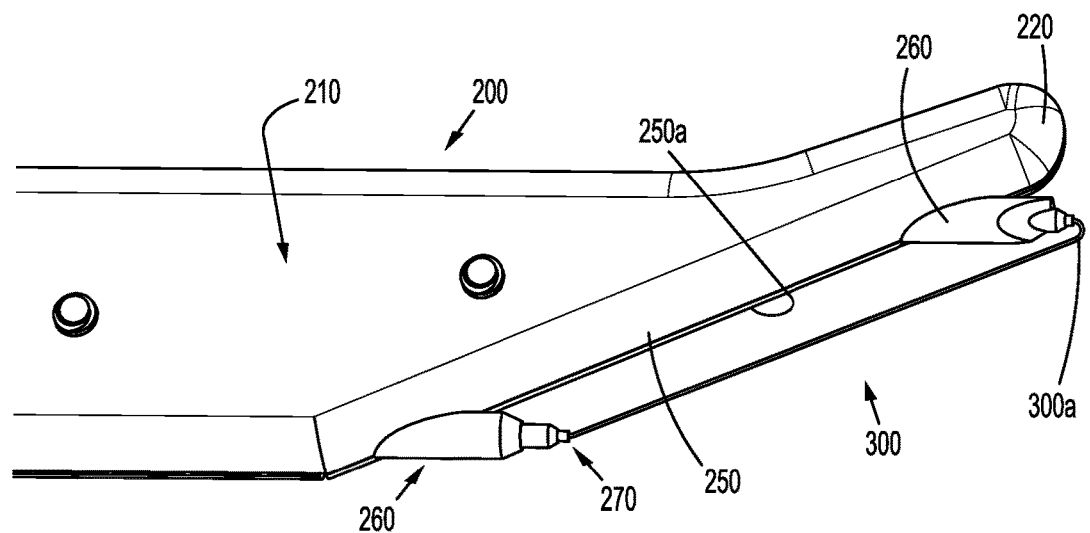
FIG. 2 is an enlarged view of the indicated area of detail of FIG. 1.

With reference to FIGS. 1 and 2, the electrosurgical device 100 includes a body portion 110 and a tool portion 200 extending distally from the body portion 110. The tool portion 200 includes a return lead 210 electrically coupled to the electrosurgical energy source (e.g., via a return terminal) and an active lead 300 electrically coupled to the electrosurgical energy source (e.g., via an active terminal). The body portion 110 includes a switch 120 to control electrical communication between the supply line 112 and the active lead 300 of the tool portion 200 for selectively activating the active lead 300 to cut tissue. The return lead 210 serve as an electrical return for electrosurgical energy (e.g., electric current) conducted through the active lead 300.

With particular reference now to FIG. 2, the return lead 210 may be formed of, e.g., stainless steel. In particular, a large surface area of the return lead 210 may provide a desirable ratio of return surface area to cutting surface area for high efficiency in cutting tissue. The return lead 210 includes a nose portion 220 configured to engage tissue, and an anchoring portion 250 defining an acute angle with respect to a longitudinal axis "L-L" (FIG. 1) defined by the body portion 110. The nose portion 220 is disposed at, e.g., a distal-most portion, of the return lead 210. The nose portion 220 may be laterally offset from the longitudinal axis "L-L" defined by the body portion 110. The nose portion 220 may include a blunt tip to reduce damage or trauma to tissue. The anchoring portion 250, as noted above, defines, e.g., an acute angle, with respect to the longitudinal axis "L-L." The anchoring portion 250 is configured to support the active lead 300.

The tool portion 200 further includes a pair of insulators 260 configured to electrically insulate the active lead 300 from the return lead 210. Each insulator 260 may have a tubular configuration defining a bore therethrough. Under such a configuration, the insulators 260 may be disposed on opposing end portions of the anchoring portion 250 such that one of the insulators 260 is disposed adjacent the nose portion 220 of the return lead 210 and the other insulator 260 is disposed adjacent a proximal-most end of the anchoring portion 250. In embodiments, the return lead 210 may define bores or openings (not shown) configured to securely support respective insulators 260 therein. In particular, the insulators 260 may be secured with the return lead 260 such that the insulators 260 are substantially parallel to the longitudinal axis "L-L." In an embodiment, the insulators 260 are oriented to provide a constant gap between the active lead 300 and a surface 250a of the anchoring portion 250 that defines the acute angle with the longitudinal axis "L-L."

In embodiments, the insulators 260 may be formed of a ceramic material due to its hardness and inherent ability to withstand high temperature fluctuations. Alternatively, the insulators 260 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

With continued reference to FIG. 2, the tool portion 200 further includes supports s 270 configured to support the active lead 300 therethrough. The supports 270 are secured within the respective insulators 260. Each support 270 may be, e.g., a hypotube, formed of stainless steel. In an embodiment, the supports 270 may be axially aligned with the respective insulators 260.

With continued reference to FIG. 2, the active lead 300 may be formed of a single strand metal wire such as, e.g., tungsten wire, that extends through the supports 270. In particular, a portion 300a of the active lead 300 extending out of the support 270 adjacent the nose portion 220 is directed towards the support 270 in a proximal portion of the anchoring portion 250 of the return lead 210, while maintaining a gap between the active lead 300 and anchoring portion 250. Further, the active lead 300 is spaced apart from the exterior of the insulators 260. A portion of the active lead 300 extending between the insulators 260 may be, e.g., substantially parallel with the surface 250a of the anchoring portion 250 defining the acute angle with respect to the longitudinal axis "L-L." The active lead 300 may be in tension such that when the active lead 300 engages tissue, the active lead 300 does not deflect or sag while cutting tissue.

In use, a clinician may position the electrosurgical device 100 adjacent a target tissue. In order to cut tissue from a surgical site, the electrosurgical device 100 is activated by actuating the switch 120 to supply electrosurgical energy to the active lead 300. Activation of the electrosurgical device 100 draws the electrosurgical energy from the electrosurgical energy source to the active lead 300. The nose portion 220 is configured to facilitate plunge cutting. The nose portion 220 is configured to contact tissue at approximately the same time as, e.g., the portion 300a of the active lead 300, and thus performing a cut in tissue. The return lead 210 returns the electrosurgical energy to the electrosurgical energy source via the return terminal of the electrosurgical energy source. Under such a configuration, the electrosurgical energy applied via the active lead 300 across tissue severs the tissue. This process may be repeated as necessary. After tissue is removed, the clinician may coagulate and/or cauterize the tissue to control bleeding.

Figure 3:
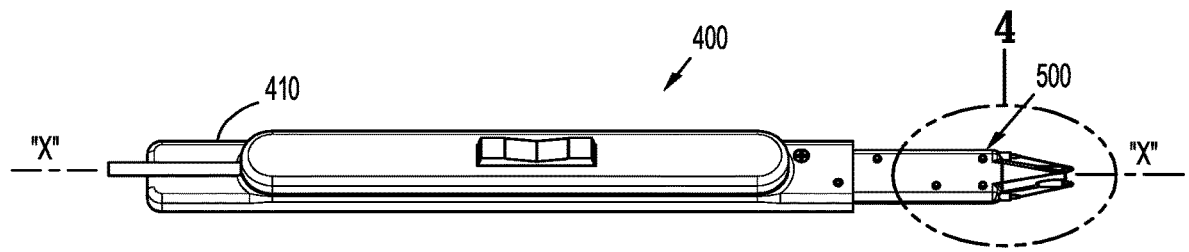
FIG. 3 is a perspective view of an electrosurgical device in accordance with another aspect of the present disclosure.
Figure 4:
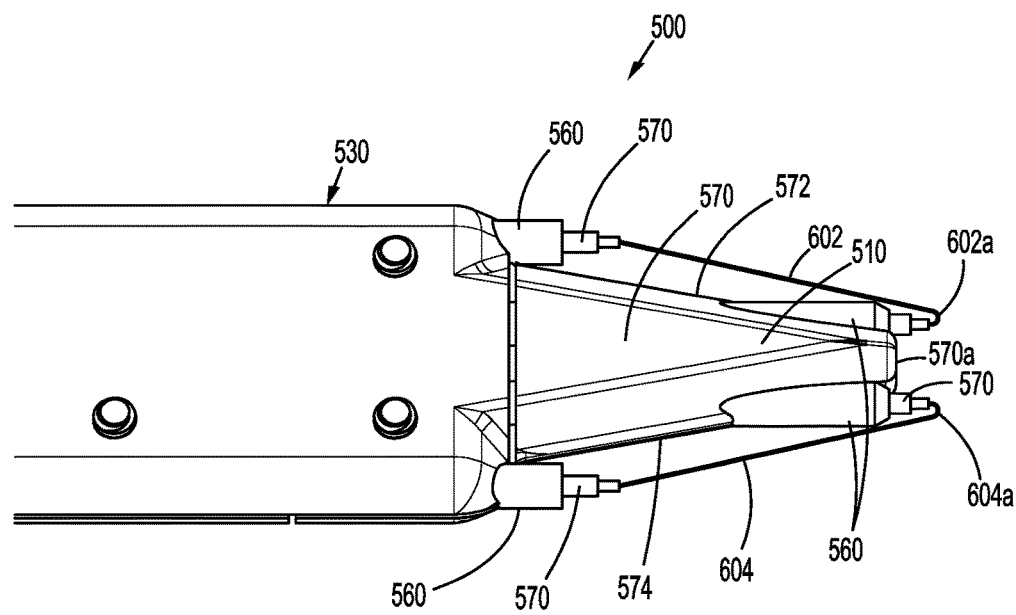
FIG. 4 is an enlarged view of the indicated area of detail of FIG. 3.

With reference now to FIGS. 3 and 4, there is provided an electrosurgical device 400 in accordance with another aspect of the present disclosure. In the interest of brevity, portions of the electrosurgical device 400 substantially similar to the portion of the electrosurgical device 100 (FIGS. 1-2) will not be described herein to avoid obscuring the present disclosure in unnecessary detail. The electrosurgical device 400 includes a body portion 410 and a tool portion 500 extending distally from the body portion 410. The tool portion 500 includes a return lead 510 and active leads 602, 604 configured to cut tissue. In particular, the return lead 510 is adapted to be electrically coupled to the return terminal of the electrosurgical energy source (not shown) such that the return lead 510 serve as an electrical return for electrosurgical energy (e.g., electric current) conducted through the active leads 602, 604. The active leads 602, 604 are coupled to the active terminal of the electrosurgical energy source.

The return lead 510 may be formed of, e.g., stainless steel. In particular, a large surface area of the return lead 510 compared to the active leads 602, 604 may provide a desirable ratio of return surface area to cutting surface area for high efficiency in cutting tissue. The return lead 510 includes a base portion 530 coupled to the body portion 410 of the electrosurgical device 400, and a tapered portion 570 including opposing surfaces 572, 574 defining respective, e.g., acute angles, with respect to a longitudinal axis "X-X" defined by the electrosurgical device 400. A first pair of insulators 560 is disposed on opposing peripheral portions of the base portion 530 and a second pair of insulators 560 is disposed on a distal portion 570a of the tapered portion 570. In this manner, the opposing active leads 602, 604 are disposed in registration with respective opposing surfaces 572, 574 of the tapered portion 570. As discussed hereinabove with respect to the electrosurgical device 100 (FIGS. 1-2), each insulator 560 has a support 570 configured to securely support the corresponding active leads 602, 604 therethrough. The insulators 560 and the supports 570 are substantially similar to the insulators 260 and the supports 270 respectively. Under such a configuration, each of the active leads 602, 604 are spaced apart and insulated from the return lead 510.

The active leads 602, 604 are provided on opposing sides of the tool portion 500. Under such a configuration, the clinician need not rotate the tool portion 500 or re-grip the body portion 410 to cut tissue on opposing sides of the surgical site, thereby facilitating cutting of tissue in various directions and orientations. In embodiments, the tapered portion 570 may be monolithically formed of stainless steel. Accordingly, any portion of the return lead 510 may serve as an electrical return for electrosurgical energy (e.g., electric current) conducted through the active leads 602, 604. For example, the distal portion 570a of the tapered portion 570 may contact tissue at approximately the same time as, e.g., at least one of the distal portions 602a, 604a, of the active leads 602, 604, and thus allowing it to cut. The return lead 510 returns the electrosurgical energy to the electrosurgical energy source. In this manner, the electrosurgical energy applied via the active leads 602, 604 across tissue severs tissue in contact with either or both of the active leads 602, 604. The use and operation of the electrosurgical device 400 is otherwise substantially similar to the use and operation of the electrosurgical device 100 (FIGS. 1 and 2) described hereinabove, and thus is not be described herein.

Figure 5:
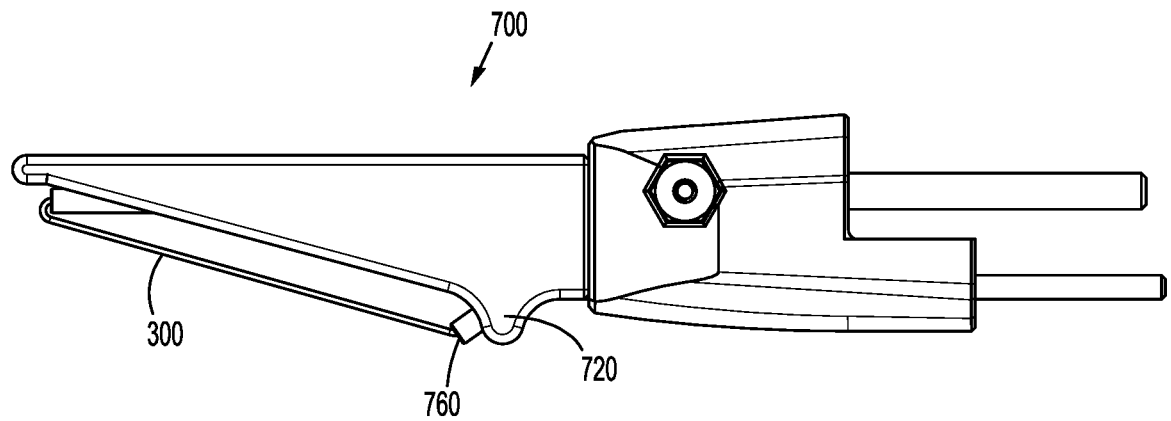
FIG. 5 is a side view of a tool portion of an electrosurgical device in accordance with another aspect of the present disclosure.
Figure 6:
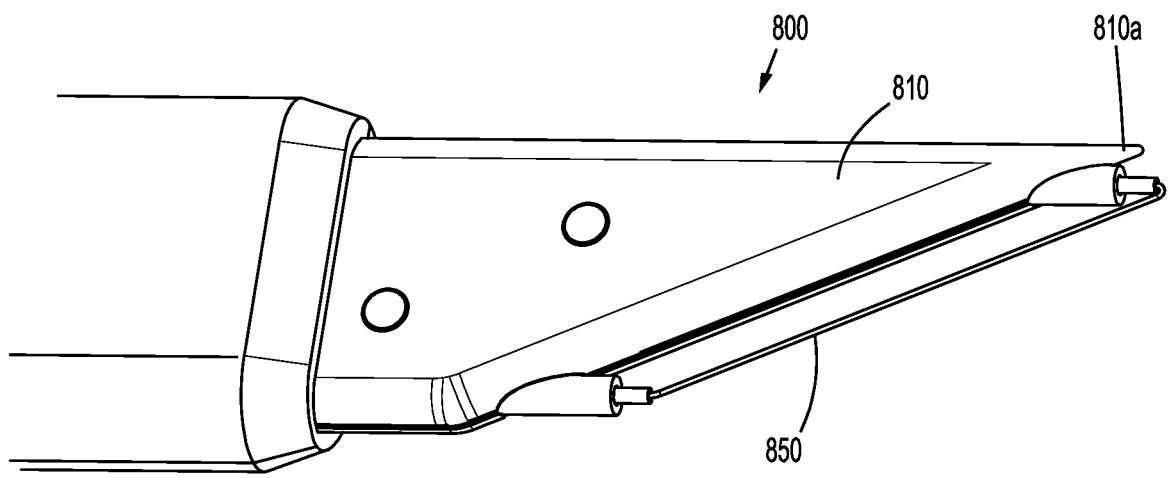
FIG. 6 is a perspective view of a tool portion of an electrosurgical device in accordance with yet another aspect of the present disclosure.

Referring to FIG. 5, while the electrosurgical device 100 has the nose portion 220 (FIG. 2) disposed adjacent the distal insulator 260, it is contemplated that an electrosurgical device 700 may include a nose portion 720 adjacent a proximal-most insulator 760 to facilitate contact with tissue during a surgical procedure. The nose portion 720 may have a blunt tip to reduce damage to tissue. Alternatively, as shown in FIG. 6, it is also contemplated that an electrosurgical device 800 may include a return lead 810 without a blunt nose portion. The return lead 810 may be monolithically formed of stainless steel. Accordingly, any portion of the return lead 810 may serve as an electrical return for electrosurgical energy (e.g., electric current) conducted through the active lead 850. For example, a distal-most tip 810a of the return lead 810 may contact tissue at approximately the same time as the active lead 850, and thus allowing it to cut tissue.

Figure 7:
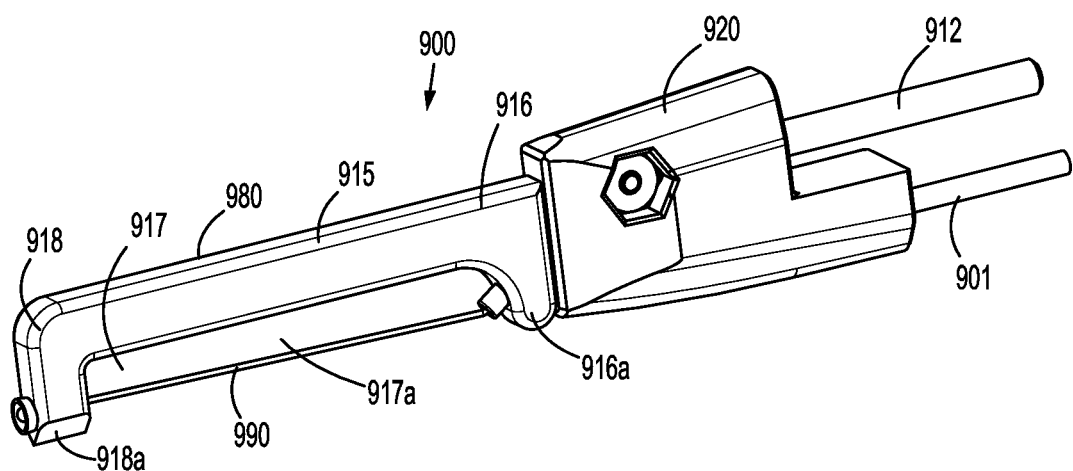
FIG. 7 is a perspective view of a tool portion of an electrosurgical device in accordance with another aspect of the present disclosure.
Figure 8:
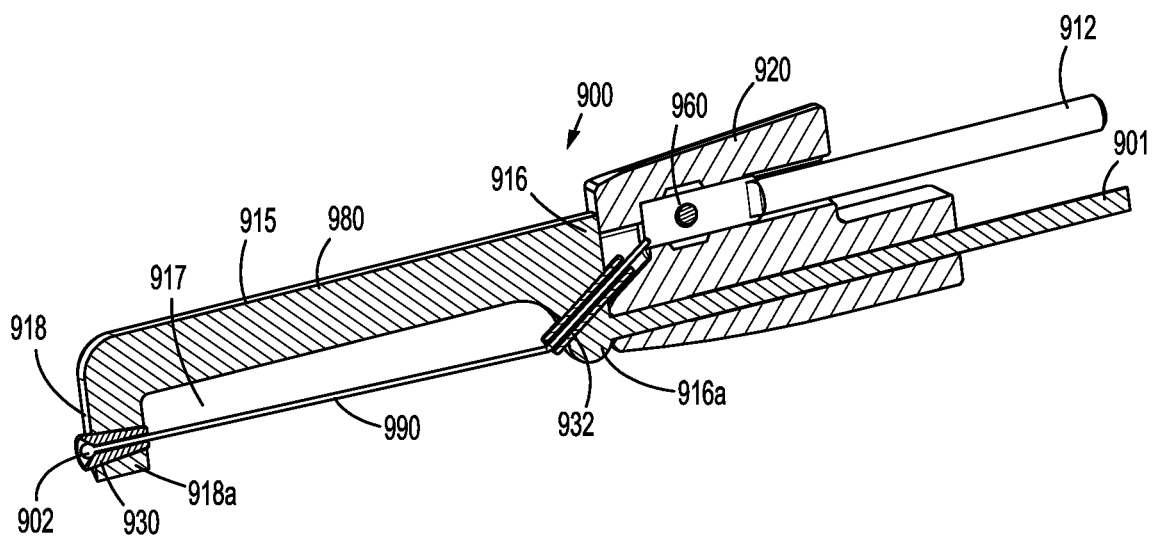
FIG. 8 is a side cross-sectional view of the tool portion of FIG. 7.

With reference now to FIGS. 7 and 8, another electrosurgical device in accordance with embodiments of the present disclosure is shown generally as an electrosurgical device 900. The electrosurgical device 900 includes a body portion 920 and a tool portion 980 extending distally from the body portion 920. The body portion 920 includes a supply line 912 configured to electrically couple an active lead 990 of the tool portion 980 with the active terminal of the electrosurgical energy source, and a return line 901 electrically coupling a return lead 915 of the tool portion 980 with the return terminal of the electrosurgical energy source. The return lead 915 may be formed of stainless steel as a single construct or, alternatively, monolithically formed of stainless steel. In particular, the return lead 915 defines, e.g., a U-shaped, cavity 917 configured to receive the active lead 990 extending therein such that the active lead 990 and the return lead 915 define a gap 917a therebetween. In particular, the active lead 990 is supported on proximal and distal portions 916, 918 of the return lead 915. In particular, proximal and distal portions 916, 918 may define respective bores configured to securely receive insulators 932, 930, respectively. The insulators 930, 932 are configured to electrically insulate the active lead 990 from the return lead 915. In particular, the insulator 930 is secured with the distal portion 918 of the return lead 915 and has a conical profile that defines a bore therethrough. The insulator 932 has a tubular configuration to receive the active lead 990 therethrough.

Figure 9:
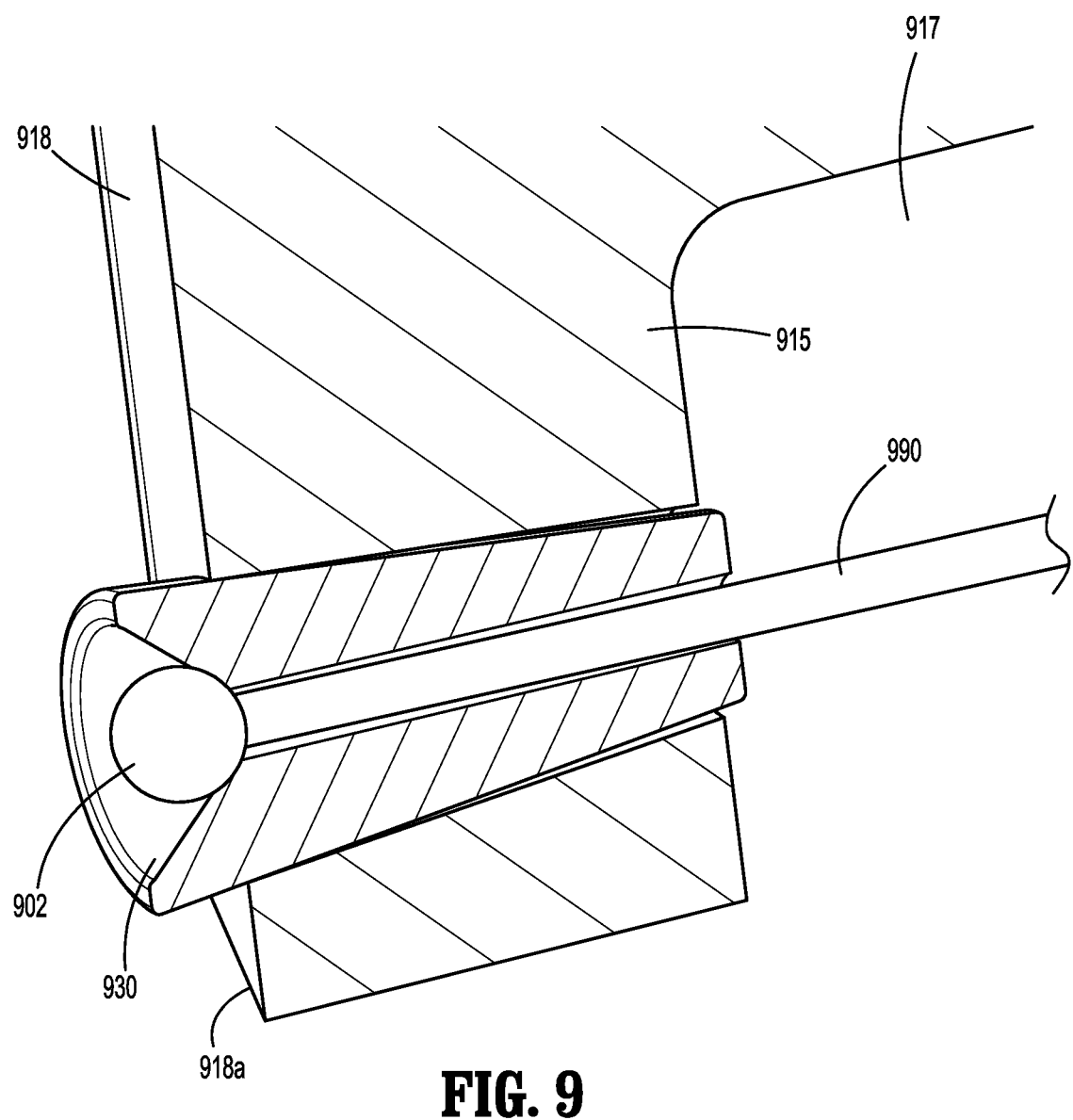
FIG. 9 is a partial cross-sectional view of a distal portion of the tool portion of the electrosurgical device of FIG. 8.

With particular reference to FIGS. 8 and 9, the active lead 990 is a wire, e.g., a single strand of tungsten wire. Small surface area of the wire provides high efficiency in cutting tissue. The active lead 990 includes a distal end portion including a ferrule 902 configured to be received in the insulator 930 and a proximal end portion coupled to a tensioner 960 in the body portion 920. By placing the ferrule 902 within the insulator 930 having the conical profile, the tension of the active lead 990 may be adjusted by rotating the tensioner 960. The tensioner 960 may be, e.g., a screw, rotatably adjusting the tension in the active lead 990. Under such a configuration, rotation of the tensioner 960 enables the clinician to adjust the tension in the active lead 990. The insulator 932 has a tubular profile defining a lumen through which the active lead 990 may extend without coming into contact with the return lead 915.

With continued reference to FIG. 8, the distal portion 918 of the return lead 915 includes a sharp leading edge 918a forming a blade (FIG. 7) to further facilitate cutting of tissue when the leading edge 818a and the active lead 990 contact tissue. The proximal portion 916 of the return lead 915 may also include a nose portion 916a having a blunt tip. The nose portion 916a is configured to facilitate engagement of the return lead 915 with tissue to facilitate cutting of tissue when the nose portion 916a and the active lead 990 engage tissue. It is contemplated that the electrosurgical device 900 may be configured without the tensioner 960. For example, the proximal end of the active lead 990 may include a loop and the body portion 9220 may include a hook electrically coupled with the supply line 912 such that the loop of the active lead 990 is placed on the hook. It is also contemplated that other configurations may be utilized to support the active lead 990 on the return lead 915. For example, the active lead 990 may be supported by a plurality of insulator plates. For example, three ceramic or glass plates may be stacked such that the plates are offset from each other to define a peripheral groove between the two outer plates to support the active lead 990 in the groove. Outer surfaces of the stacked insulator plates may be provided with return leads such as, e.g., stainless steel plates, that are screwed on together. It is further contemplated that an O-ring may be provided between the insulator plate and the return lead to provide a fluid seal therebetween.

Figure 10:
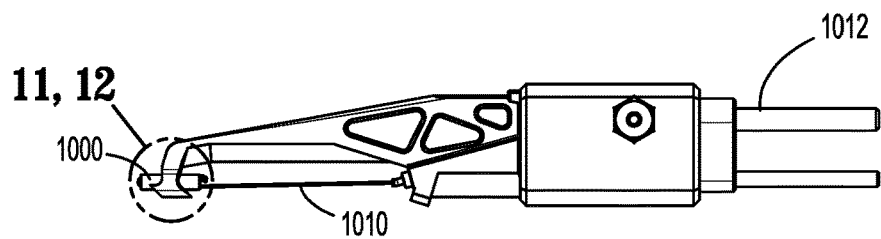
FIG. 10 is a side view of a tool portion of another electrosurgical device in accordance with another aspect of the present disclosure.
Figure 11:
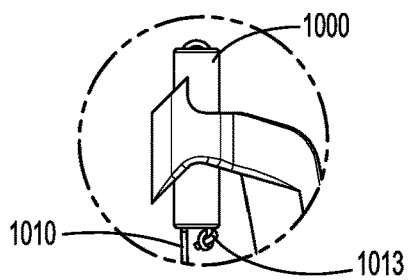
FIG. 11 is an enlarged view of the indicated area of detail of FIG. 10.
Figure 12:
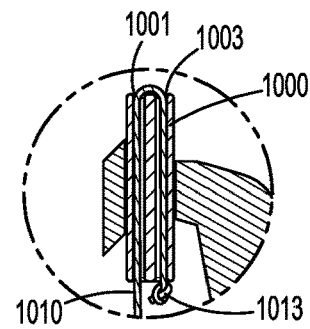
FIG. 12 is a side cross-sectional view of the indicated area of detail of FIG. 10.
Figure 13:
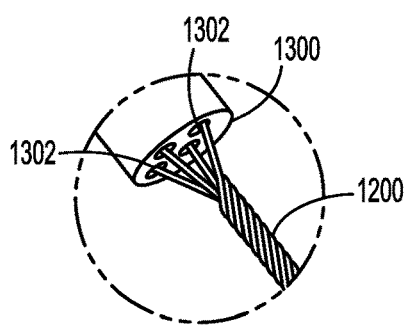
FIG. 13 is a perspective view of an insulator in accordance with another aspect of the present disclosure.
Figure 14:
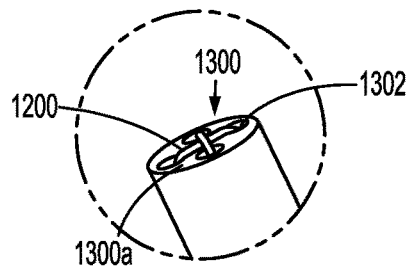
FIG. 14 is a partial perspective view of the insulator of FIG. 13 illustrating a distal end of the insulator.
Figure 15:
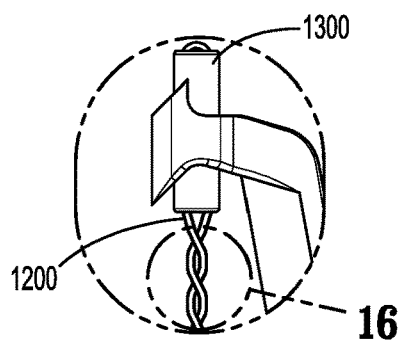
FIG. 15 is a side view of the insulator of FIG. 14 illustrating use with a return lead.
Figure 16:
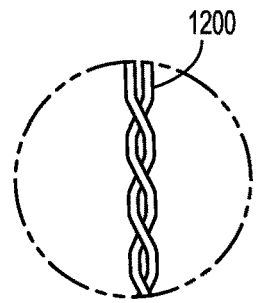
FIG. 16 is an enlarged view of the indicated area of detail of FIG. 15.

With reference now to FIGS. 10-12, there is illustrated an insulator 1000 for use with an electrosurgical device, e.g., the electrosurgical devices 100, 400, 700, and/or 900 (FIGS. 1-2, 3-4, 5, and/or 7-9, respectively), in accordance with embodiments of the present disclosure. The insulator 1000 may be an electrical insulator formed of, e.g., ceramic, or an electrical and thermal insulator. The insulator 1000 defines a pair of bores 1001, 1003 configured to receive the active lead 1010 therethrough. One end of the active lead 1010 may include a knot or a ferrule 1013 having dimensions larger than an opening of at least one of the bores 1001, 1003, such that when the active lead 1010 is looped around the bores 1001, 1003, the knot or ferrule 1013 secures the one end of the active lead 1010 to the insulator 1000. The other end of the active lead 1010 is electrically coupled to the supply line 1012.

With reference now to FIGS. 13-16, it is also contemplated that an active lead for use with an electrosurgical device, e.g., the electrosurgical devices 100, 400, 700, and/or 900 (FIGS. 1-2, 3-4, 5, and/or 7-9, respectively), may include a plurality of wires. For example, instead of a single strand wire, an active lead 1200 may be a braided wire formed of plurality of strands. To this end, an insulator 1300 in accordance with embodiments of the present disclosure may define a plurality of bores 1302 each configured to receive one strand of the plurality of strands. For example, a distal end 1300a of the insulator 1300 may receive the plurality of strands through the bores 1302 in a crisscross manner to form a braided active lead 1200. For example, a diameter of the active lead 1200 may be in a range of about 0.002 inch and about 0.004 inch.

Figure 17:
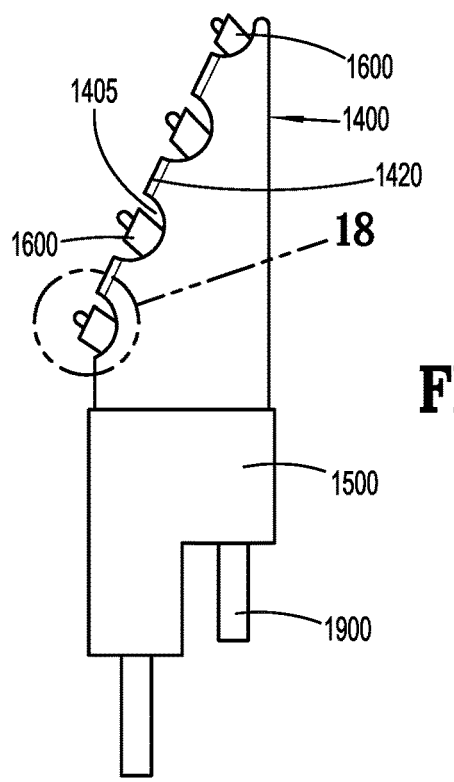
FIG. 17 is a side view of a tool portion of an electrosurgical device in accordance with another aspect of the present disclosure.
Figure 18:
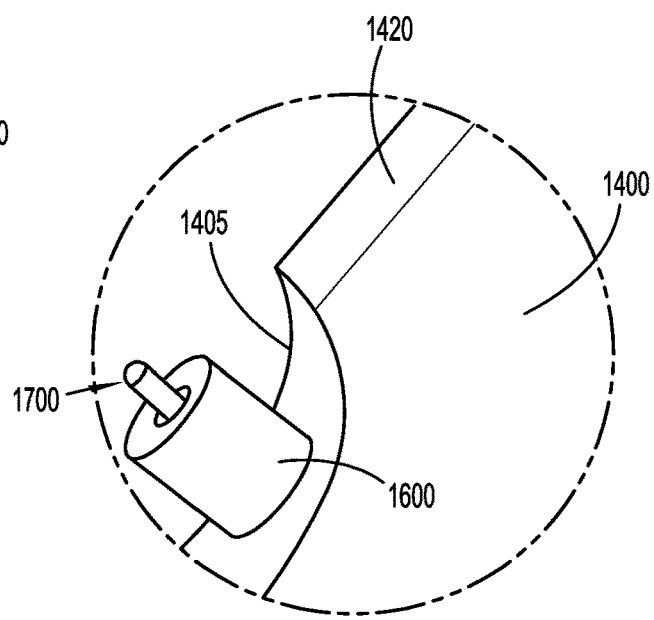
FIG. 18 is an enlarged view of the indicated area of detail of FIG. 17.
Figure 19:
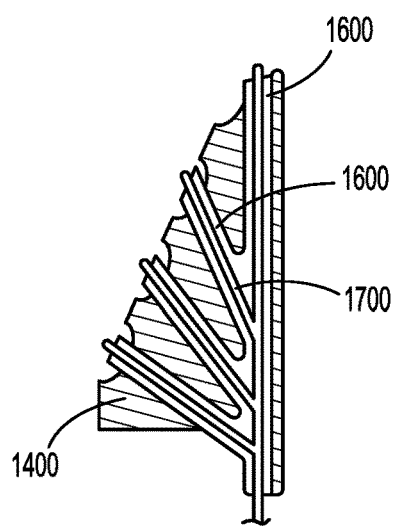
FIG. 19 is a side cross-sectional view of the tool portion of the electrosurgical device of FIG. 18.

With reference now to FIGS. 17-19, while the active leads 300, 602, 604, 850, 990, 1010, 1200 have been shown as a wire, it is further contemplated that an active lead in accordance with embodiments of the present disclosure may include a plurality of contact points arranged in a linear fashion to form a cutting line to cut tissue with electrosurgical energy supplied thereto. A return lead 1400 extends distally from a body portion 1500 and defines a plurality of recesses 1405 arranged in a linear fashion. Each recess 1405 includes an insulator 1600 configured to support a portion the active lead 1700. A portion of the return lead 1400 disposed between adjacent recesses 1405 forms a blade edge 1420 configured for mechanical cutting of tissue. Under such a configuration, the plurality of active leads 1700 protruding through the respective openings of the insulators 1600 and the blade edges 1420 are arranged in a linear fashion, thereby defining a cutting line. With particular reference to FIG. 19, the plurality of insulators 1600 extends through the return lead 1400. However, the plurality of active leads 1700 converges within the return lead 1400 to be coupled with the supply line 1900. The use of the active lead 1700 is substantially similar to the above-described return leads, and thus is not be described herein. Under such a configuration, a large surface area of the return lead 1400 may provide a desirable ratio of return surface area to cutting surface area for high efficiency in cutting tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical device for cutting tissue comprising:
    a body portion; and
    a tool portion extending distally from the body portion, the tool portion defining a longitudinal axis, the tool portion including:
        a return lead adapted to be electrically coupled to a return terminal of an electrosurgical energy source, the return lead including a distal surface and a planar surface extending from the distal surface to a distal end of the body portion;
        first and second electrical insulators disposed on the distal surface of the return lead, the first electrical insulator disposed distal of the second electrical insulator; and
        an active lead adapted to be electrically coupled to an active terminal of the electrosurgical energy source, the active lead extending through the first and second electrical insulators such that a gap is defined between the active lead and the distal surface of the return lead, wherein upon activation of the electrosurgical energy source, electrosurgical energy is transmitted from the active lead through the tissue to the return lead to cut the tissue.

2. The electrosurgical device according to claim 1, wherein the distal surface of the return lead defines an acute angle with respect to the longitudinal axis of the tool portion.

3. The electrosurgical device according to claim 1, wherein the first and second electrical insulators are parallel to the longitudinal axis of the tool portion.

4. The electrosurgical device according to claim 1, wherein the return lead includes a nose portion configured to engage the tissue, the nose portion adjacent the second electrical insulator.

5. The electrosurgical device according to claim 4, wherein the nose portion includes a blunt tip.

6. The electrosurgical device according to claim 1, wherein the active lead is a wire.

7. The electrosurgical device according to claim 1, wherein the active lead is a single strand wire.

8. The electrosurgical device according to claim 1, wherein the first or second electrical insulator has a tubular configuration.

9. The electrosurgical device according to claim 1, wherein the first or second electrical insulator is formed of ceramic.

10. The electrosurgical device according to claim 1, wherein the return lead is formed of stainless steel.

11. The electrosurgical device according to claim 1, wherein the tool portion further includes first and second supports configured to be securely received in the respective first and second electrical insulators, the first and second supports configured to support the active lead.

12. The electrosurgical device according to claim 4, wherein the nose portion is disposed distal to at least a portion of the active lead.

13. The electrosurgical device according to claim 1, wherein the active lead extends parallel to the distal surface of the return lead.

14. The electrosurgical device according to claim 1, wherein the first and second electrical insulators extend distally from the distal surface of the return lead to define an obtuse angle with respect to the distal surface of the return lead.

15. The electrosurgical device according to claim 1, wherein a surface area of the return lead is larger than a surface area of the active lead.

16. An electrosurgical device for cutting tissue, comprising:
a body portion; and
a tool portion extending distally from the body portion, the tool portion defining a longitudinal axis, the tool portion including:
a return lead configured to electrically couple to an electrosurgical energy source, the return lead having a distal surface defining an acute angle with respect to the longitudinal axis of the tool portion and a planar surface extending from the distal surface of the return lead to a distal end of the body portion;
first and second electrical insulators extending distally from the distal surface of the return lead; and
an active lead extending through the first and second electrical insulators and configured to electrically couple to the electrosurgical energy source for cutting the tissue, the active lead extending between the first and second electrical insulators parallel to and spaced from the distal surface of the return lead.

17. The electrosurgical device according to claim 16, wherein the first electrical insulator is disposed distal of the second electrical insulator.

18. The electrosurgical device according to claim 16, wherein a surface area of the return lead is larger than a surface area of the active lead.

19. The electrosurgical device according to claim 16, wherein the first and second electrical insulators extend from the distal surface of the return lead parallel to the longitudinal axis defined by the tool portion to define an obtuse angle with respect to the distal surface of the return lead.

20. An electrosurgical device for cutting tissue, comprising:
a body portion; and
a tool portion extending distally from the body portion, the tool portion defining a longitudinal axis, the tool portion including:
a return lead configured to electrically couple to an electrosurgical energy source, the return lead including:
a distal surface defining an acute angle with respect to the longitudinal axis of the tool portion;
a planar surface extending from the distal surface of the return lead to a distal end of the body portion; and
a nose portion extending distal to the distal surface of the return lead and configured to engage the tissue;
a pair of electrical insulators extending distally from the distal surface of the return lead parallel to the longitudinal axis of the tool portion; and
an active lead extending through the pair of electrical insulators and configured to electrically couple to the electrosurgical energy source for cutting the tissue, the active lead having a surface area less than a surface area of the return lead.

* * * * *